United States Patent [19]

Pace et al.

[11] Patent Number: 4,462,409
[45] Date of Patent: Jul. 31, 1984

[54] PRESSURE TRANSDUCER DOME

[75] Inventors: Max L. Pace, Deer Park; Fred J. Shipley, Pearland; Jerald H. Webb, Seabrook, all of Tex.

[73] Assignee: Healthdyne, Inc., Marietta, Ga.

[21] Appl. No.: 263,890

[22] Filed: May 15, 1981

[51] Int. Cl.³ .............................................. A61B 5/02
[52] U.S. Cl. .................................. 128/675; 128/748; 73/706
[58] Field of Search .............................. 128/673–675, 128/748, 672; 73/706

[56] References Cited

U.S. PATENT DOCUMENTS

| | | | |
|---|---|---|---|
| 3,631,850 | 1/1972 | Levasseur | 128/675 |
| 3,818,765 | 6/1974 | Ericksen | 128/675 X |
| 3,865,100 | 2/1975 | Kanai et al. | 128/675 |
| 3,880,151 | 4/1975 | Nilsson et al. | 128/673 |
| 4,072,056 | 2/1978 | Lee | 128/675 |
| 4,291,701 | 9/1981 | Bowman | 128/675 |
| 4,365,635 | 12/1982 | Bowman | 128/675 |

Primary Examiner—Kyle L. Howell
Assistant Examiner—John C. Hanley
Attorney, Agent, or Firm—Browning, Bushman, Zamecki & Anderson

[57] ABSTRACT

A pressure transducer for use in a direct blood pressure measuring system includes a domed portion which is connected to a line interposed in a patient's blood supply system. A sterile solution serves to interface the patient's blood system and the pressuring measuring apparatus. An asymmetrical configuration of the interior cavity in the domed portion of the transducer, which cavity is in the fluid flow path, as well as a convex surface formed on the top face of the cavity improve the reliability of the transducer by avoiding standing waves and bubbles in the fluid in the cavity. Flow lines intersecting the cavity are tapered to improve impedance matching with the cavity.

14 Claims, 2 Drawing Figures

PRESSURE TRANSDUCER DOME

BACKGROUND OF THE INVENTION

The present invention relates to pressure measuring apparatus and more particularly to pressure measuring apparatus for use in cardiovascular direct fluid pressure measuring systems.

Direct blood pressure measurement in the cardiovascular system of a patient encounters a particular problem relating to the occurrence of bubbles in the measuring apparatus. Such apparatus typically includes flow lines and associated apparatus such as syringes, transducers, valves and the like. This equipment is normally made of highly transparent plastic materials which permit the observance of the formation and accumulation of air bubbles in fluids therein. Air bubbles may be formed by fluid flowing past structural features forming impediments in the fluid flow system. Such impediments may be in the form of sharp corners, or any feature, for that matter, which causes turbulence in the fluid flow to thereby entrain air bubbles in the fluid. Again, corners, pockets or the like, in the flow path through such equipment can be a likely place for bubbles to accumulate. Therefore, such equipment is designed to limit, to the extent possible, such structural features.

Systems for the direct measurement of blood pressure of a medical patient normally employ an arterial catheter inserted into an artery or vein and extending therein to the point of measurement. A fluid flow line connects the catheter to a manifold system. The manifold utilizes a syringe to inject a sterile transmitting fluid into the pressure measuring system. A transducer, also connected to the manifold, provides a means for converting the pressure state of the transmitting fluid into an electrical signal for providing intelligible data. If bubbles are formed and accumulate in any of the fluid flow portions of the above described system, serious problems may result which can adversely affect not only the accuracy of the pressure measurements but also the well being and perhaps the life of the patient being monitored.

The pressure measuring system described above utilizes a sterile transmitting fluid in the system which actually interfaces at one point directly with the blood flowing in the cardiovascular system of the patient. A variety of flow lines and interconnecting valves communicate this transmitting fluid with the transducer. This system, therefore, directly transmits the patient's blood pressure to the transmitting fluid which connects the pressure with the transducer. Such a system assumes that the transmitting fluid is non-compressible. However, if air bubbles exist in the transmitting fluid, this assumption is incorrect and consequently errors will occur in the data reading out of the transducer. A large bubble in the system can create errors, for example, in the range of 10 to 20%. The readout of such equipment is usually in a pressure-versus-time format, and such errors thus change the frequency response of the system, which in turn is reflected in the damping and distortion of a waveform being displayed on a visual monitoring device. Such errors are of sufficient nature to perhaps change the diagnosis of a patient's condition which may result in an erroneous disposition of his treatment.

Another aspect of the problems with air bubbles in such a system may result when a fluid is injected into the cardiovascular system. This may occur when the transmitting fluid of the pressure measuring system described above is injected by the syringe into the fluid flow system. Any air bubbles entrained in the fluid could be transmitted directly into the patient's cardiovascular system, giving rise to the danger of air embolism which may create turbulence and even disruption of blood flow. This, of course, can be a life threatening situation.

In order to avoid as much as possible the problems and dangers associated with air bubble entrainment in fluid flow systems of this sort, those parts of the systems which are subject to the occurrence of bubbles are manufactured from a transparent material. This is accomplished, for example, by using highly polished dies in plastic extruding or injection molding equipment. By rendering the surface as smooth as possible, the transparency of the materials used in manufacture is maximized. This in turn permits observation of the fluid for detecting bubbles, which may then be dissipated as by tapping or jarring the equipment. It has also been thought that by minimizing disturbances in the fluid flow path, the chance of creating turbulance is decreased. This then would lessen the chance of creating air bubbles.

The transducer used in such systems generally comprises a cylindrical housing having top and bottom chamber portions separated by a flexible membrane. A dome is arranged over the top of the membrane and has a cavity formed therein to form the top chamber. This top chamber is connected by means of ports in the dome walls to the fluid flow lines of the pressure measuring system. The bottom chamber houses a strain gage or the like which is positioned against the bottom surface of the membrane to detect movement of the membrane and provide an electrical signal indicative of such movement. The top chamber formed by the cavity serves as a fluid accumulator and to bring fluid into interface with the flexible membrane. Pressure fluctuations originating in a patient's cardiovascular system are transmitted by means of the transmitting fluid and the arterial catheter to the fluid flow line connecting with the manifold and transducer. Thus, the pressure pulses enter the cavity in the transducer dome where they flex the membrane which in turn produces an electrical signal for operating readout equipment.

The cavity within the transducer dome has been heretofore constructed with smooth surfaces, free of corners and irregularities, and generally forming a symmetrical chamber about a flexible membrane. However, it is now found that the fluid dynamics of the top chamber cavity in the dome structure described above may produce standing waves in response to pressure pulses. The fluid dynamics of the system relate to impedance matching between various components, and to the potential for setting up standing waves. The present invention is concerned with, among other things, the fluid impedance offered by the dome portion of a pressure transducer in cardiovascular direct pressure measuring systems. If the impedances of the input and output tubes are not matched to the impedance of the dome cavity at the points of entry of the tubes into the cavity, an incoming pressure pulse into the dome cavity will be reflected back toward the source, thus producing a standing wave within the cavity. Additionally, a portion of the wave energy incident to the cavity will be reflected rather than enter the cavity. Subsequent incoming pressure pulses will strike the standing wave and will either add or substract depending on the phase between the waves. A symmetrical cavity or chamber will develop and offer a resonate enclosure for standing waves. If standing waves are present in the cavity, the behavior of the membrane and strain gage may not truly reflect the pressure in the cardiovascular system to be measured; rather, false pressure readings may be observed, whether too high or too low.

It is therefore an object of the present invention to provide a new and improved fluid pressure measuring system with features for eliminating the presence of bubbles and standing waves in the system.

SUMMARY OF THE INVENTION

With this and other objects in view the present invention contemplates fluid pressure measuring apparatus having a housing with first and second chamber portions separated by a flexible member. The second chamber houses a device for positioning against the bottom surface of the flexible member to detect movement of the member in response to pressure pulses entering the upper chamber. The first chamber is formed by a cavity formed in a generally dome shaped cover portion which is arranged over the flexible member. The cavity serves as a fluid accumulator to provide a confined volume of fluid over the flexible member and thereby transmit pressure changes, incoming to the cavity, to the flexible member. The cavity is arranged to be asymmetrical to reduce the occurrence of standing waves.

One asymmetrical feature of the cavity is the non-parallel interior side wall portions.

Another asymmetrical feature of the cavity is a sloping upper interior face of the cavity.

Still another feature of the cavity is a convex, downwardly-depending surface toward the center of the upper interior face of the cavity, acting as a fluid flow dispersing means.

Still another feature of the dome cover is the arrangement of ports or passage entrances into and out of the cavity, wherein such ports, usually a pair, are arranged on substantially opposite sides of the upper interior of the cavity and are sized to provide a closer impedance match between the ports, with their connecting fluid flow tubes, and the cavity itself.

DETAILED DESCRIPTION OF THE PREFERRED EMBODIMENTS

Figure 1:
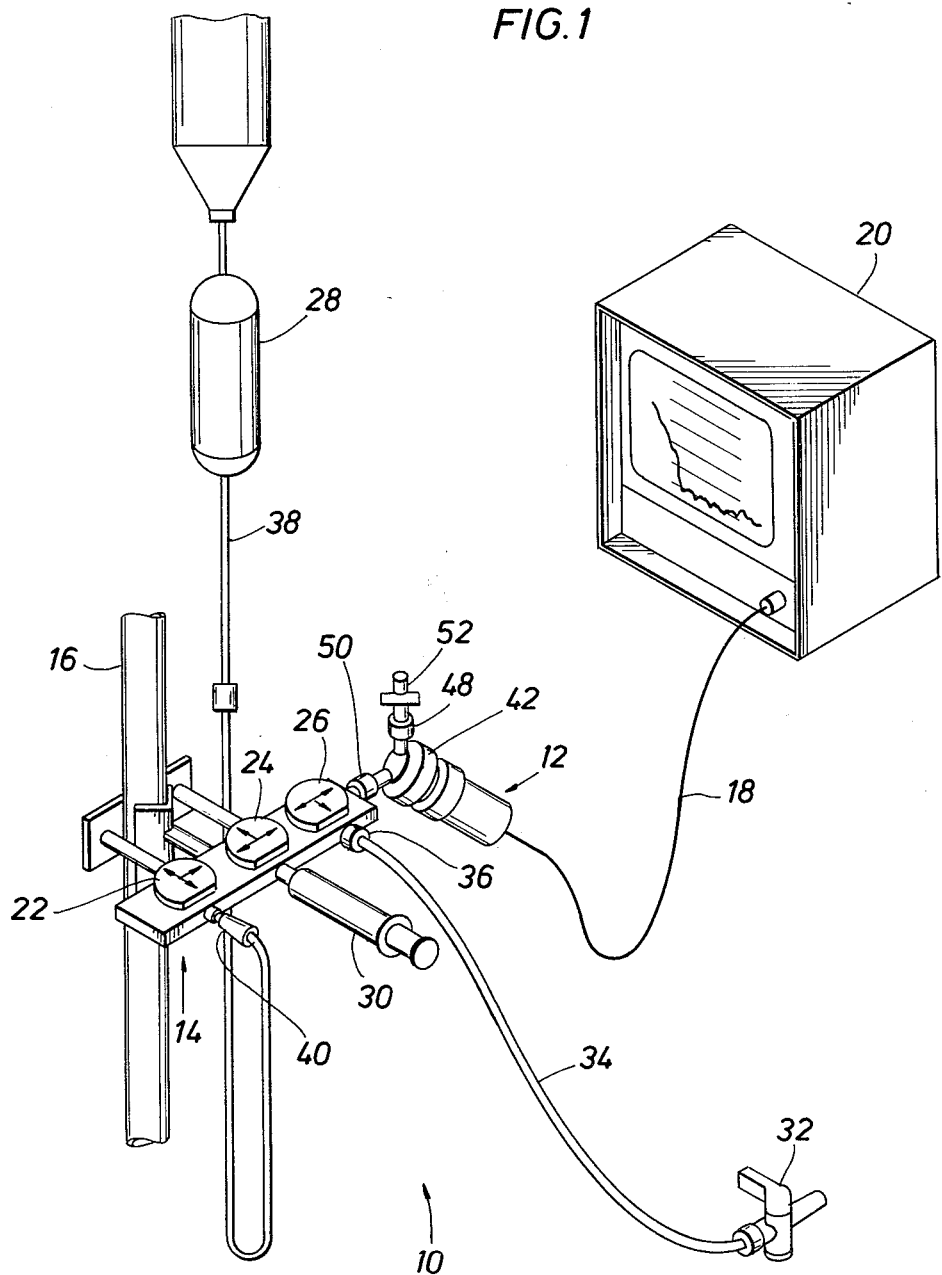
FIG. 1 is a schematic illustration, in perspective view, of a direct blood pressure measuring system incorporating a pressure transducer and pressure measuring apparatus in accordance with the present invention, and is taken in part from page 165, *Medical Instrumentation for Health Care* by L. Cromwell, et al, Prentice-Hall, Inc., 1976.

Referring first to FIG. 1 of the drawings, a schematic illustration of a direct blood pressure measuring system 10 shows a pressure transducer 12 connected to an infusion manifold 14, which in turn in clamped to an IV pole 16. The transducer is connected by means of an output cable 18 to a monitor 20 which provides an amplifier-display function and normally provides both numerical and waveform data. The manifold is shown having three valves 22, 24 and 26 for regulating fluid flow to and from a fluid resevoir 28, an irrigation syringe 30 and an arterial catheter stopcock 32, respectively. The valves 22, 24 and 26 are three-way valves which are open to fluid flow in the direction of arrows marked on the upper surface of each valve. A fluid flow line or pressure communication line 34 connects the stopcock 32 with a connection 36 to valve 26. A flow line 38 interconnects the bottom of resevoir 28 with an input connection 40 to valve 22. These flow lines 34 and 38 are typically constructed of small diameter, transparent plastic tubing made from materials such as polycarbonates, polyacrylates or clear PVC, for example. The syringe 30 is connected to a manifold input to valve 24. The transducer 12 has a dome 42 on its upper end, with the dome having two tubular passageways 44 and 46 (FIG. 2), extending outwardly from the dome and having fluid-tight threaded connectors 48, 50, respectively, or the like. Connector 50 connects the transducer 12 to an input to valve 26 on the manifold 14. Connector 48 is connected to a three-way stopcock 52 for flushing the dome 42.

Figure 2:
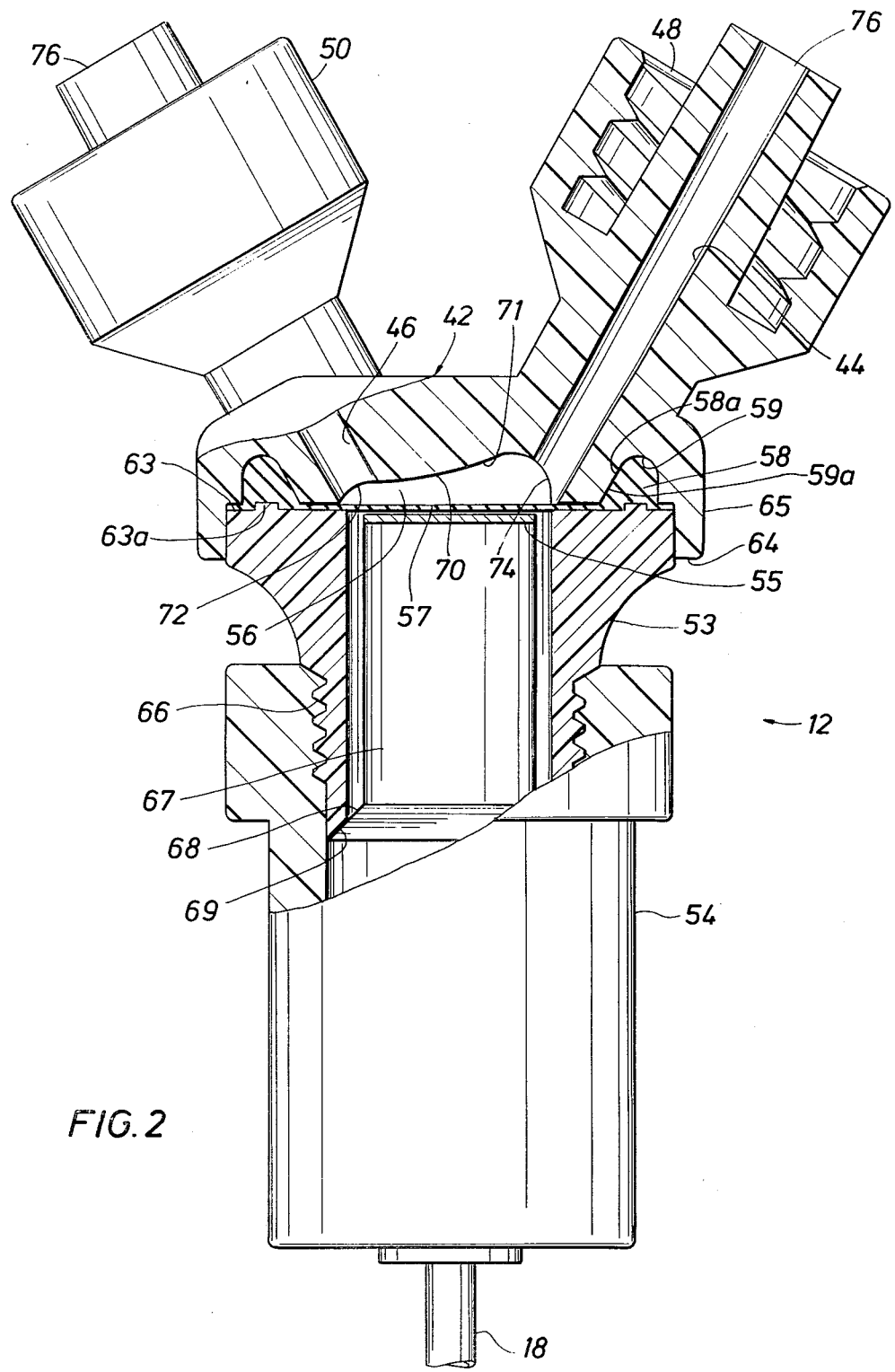
FIG. 2 is a side elevation view in partial section and partly schematic of the dome cover and upper portion of a pressure transducer in accordance with the present invention.

Referring now to FIG. 2 of the drawings, the transducer 12 includes a first housing member 53 which is coupled to the dome 42, and a second housing member 54 in which is mounted the electronic system to convert the movement of a strain gage element 55 into a usable electrical signal for transmittal by means of cable 18 to the monitor 20. The first and second housing members 53 and 54 combine to provide a chamber for containing the strain gage and related electronics and the dome 42 provides another chamber 56 for accumulating transmitter fluid. A silastic diaphragm 57 is mounted across the chamber 56 of the dome 42. The silastic diaphragm 57 has an O-ring like rim portion 58 molded on its outer peripheral edge and received within an annular groove 59 formed in the lower face of the dome 42. This rim portion 58 provides a seal between the dome 42 and the first housing member 53 to prevent the passage of fluid from one side of the diaphragm 57 to the other. As shown in FIG. 2, the radially interior annular surface portion of the groove 59 is tapered to form an annular wedge 59a, which acts on the rim 58 to tend to stretch the diaphragm 57 radially outwardly as the rim is forced into the groove by the first housing member 53 being received by the dome 42, as described hereinafter. The wedging effect of the surface portion 59a acting on the rim 58 may be enhanced by providing the rim with a tapered radially interior annular surface 58a to abut and slide along the groove surface 59a. The passageways 44 and 46 communicate with the interior cavity 56 of the dome 42 above the diaphragm 57. The bottom of the diaphragm 57 contacts the strain gage element 55.

The first housing member 53 of the transducer 12 is arranged to matingly assemble with the dome 42. The top surface 63 of the housing member 53 is sized for reception within an annular shoulder portion 64 extending downwardly from the outer cylindrical wall portion 65 of the dome 42. The housing member 53 has an energy director in the form of a low annular ridge or bead (not shown) on the outer rim of the upper surface 63 which becomes molten when subjected to ultrasonic welding techniques to bond the surface 63 with the bottom face of the dome 42 and thereby secure the assembly of the dome 42 and the first housing member 53. An annular land or ridge 63a protrudes from the surface 63 and underlies the diaphragm rim 58 to compress the rim into the dome groove 59 and insure the anchoring and sealing of the diaphragm 57 between the dome and the housing member 53.

Exterior threads 66 on the outer wall surface of first housing member 53 are arranged to receive interior mating threads on the second housing member 54 to thereby attach the member 54 to the member 53. A transducer body 67 with the strain gage element 55 mounted thereon is mounted within the second housing member 54 and received within the first housing member 53 as the two housing members are threaded together. A beveled shoulder surface 68 on the transducer body 67 is arranged to engage a complementary beveled surface 69 formed on the bottom end of housing member 53 to insure that the strain gage element 55 will be positioned relative to the diaphragm 57 to receive communication thereby of pressure fluctuations in the fluid contained within the dome cavity 56. The transducer body 67 includes the strain gage and electronics for converting movement of the strain gage element 55 into electronic signals to be displayed by the monitor 20.

Concerning the operation of the blood pressure measuring system described above, reference is again made to FIG. 1. A catheter (not shown) is inserted into an artery or vein to the point of pressure measurement, with the other end of the catheter connecting with a flow line leading to the stopcock 32. In order to make pressure measurements, a sterile solution, such as 5% dextrose in water or normal saline, is introduced into the catheter so that the fluid pressure can be transmitted directly from the cardiovascular system through the sterile solution/blood interface to the transducer 12. The resevoir 28 supplies the sterile solution to the system, with the manifold 14, the syringe 30 and the valves 22, 24 and 26 being used to first draw the solution from the resevoir and connect same with the flow line 34 to fill the pressure measuring system with the sterile solution or transmitting fluid. The transducer 12 is placed at the same height as the point of pressure measurement in the cardiovascular system by adjusting the position of the manifold 14 on the IV pole 16. This procedure reduces error due to differences in hydrostatic pressure. The transducer 12 is connected with the flow line 34 by the valve 26. Any changes in blood flow pressure will thus be transmitted through the transmitting fluid to the transducer dome 42 and thence converted by the strain gage element 55 and transducer electronics 67 to an electrical signal which is converted to useful data by the monitor 20.

An alternative direct blood pressure measuring system employing a transducer 12, including a pressure dome 42, involves connecting the flow line 34 from the cardiovascular system directly to one of the dome passages 44 and 46, and connecting the flow line 38 from the reservoir 28 directly to the other of the dome passages 44 or 46. Then, the flow lines 38 and 34 as well as the dome cavity 56 are filled with a transmitter fluid from the reservoir 28 before the catheter introduced into the cardiovascular system is connected to the flow line 34. The stopcock 32 may be utilized to clear the pressure measuring system of bubbles before the system is connected to the cardiovascular system of the patient.

Pressure fluctuations are transmitted to the dome 42 by means of one of the passages 44 or 46 whether or not the manifold 14 is included in the system. Such changes in pressure cause the diaphragm 57 to move, and the strain gage element 55 is arranged to follow such diaphragm movement. The strain gage element 55, when moved, changes the resistance in wires (not shown) included in the strain gage and electronics 67, such resistance changes being proportional to diaphragm movement which in turn is proportional to blood pressure changes. The resistance wires in the strain gage are connected in a bridge circuit which in turn is also connected with the monitor 20 by the cable 18. The monitor 20 has an amplifier function connecting with the bridge circuit. When the bridge is balanced at zero gauge pressure, voltages proportional to pressure fluctuations applied to the transducer 12 will appear at the monitor which converts the voltages to the data readout modes.

In the system just described pressure measurement depends upon the direct transmission of pressure changes through the fluid system to the transducer 12. The accuracy of such a system assumes the non-compressibility of the transmitting fluid. It is readily seen that should air bubbles be entrained in the system, such non-compressibility does not in fact exist. Bubbles in the system, therefore, boost or attenuate the pressure transmitted to the transducer 12. In one aspect, a bubble may absorb an increase in pressure being seen by the transmitting fluid. This phenomenon is known as damping, which may reduce or distort the readout, especially a waveform, to a point where completely erroneous conclusions would be drawn. This in turn could critically affect diagnosis and patient care. Bubbles in the system also pose the threat of air embolization, which, even in amounts of less than 0.5 cc, can be lethal in certain circumstances. A remedy to remove bubbles or other obstructions from the fluid flow system includes using the syringe 30 on the manifold 14 to clear the lines by flushing the system with a small amount of solution, and then resuming the pressure measuring operation. Generally, the dome 42 of the transducer is particularly susceptible of bubble formation and, therefore, one of the passages 44 or 46 on the dome usually has a three-way stopcock 52 positioned thereon for flushing this part of the system. The stopcock 52 can also be used for withdrawal of blood samples and administration of drugs. If the transducer is connected directly to the fluid reservoir 28 and the stopcock 32, the system must be open to clear bubbles therefrom by means of the stopcock, for example.

Important features of the present invention pertain to the problem of bubble formation and retention in the system. As shown in FIG. 2 of the drawings, the dome cavity 56 of dome 42 has a convex downwardly projecting portion 70 formed on the upper interior face 71 of the cavity. The convex portion 70 acts as a dispersing surface to fluids flowing across the top face 71 of the cavity 56, thus causing fluid flow to extend radially outwardly from the generally circularly shaped convex portion 70. Additionally, the upper face 71 of the dome cavity 56 does not contain any concave pockets whereby bubbles might become entrapped.

In addition to the problem of bubble formation in the system, the previously discussed problem concerning the occurrence of standing waves in the fluid dynamic system is also treated by the structure of FIG. 2. In addition to the top face 71, the dome cavity 56 is defined in part by peripheral surfaces such as 72 and 74 including the entrances to the passages 46 and 44, respectively. The surfaces 72 and 74 are sloped at different acute angles relative to the face 71 and to the diaphragm 57, as shown. In similar fashion, the interior walls about the periphery of the chamber 56 are all sloped relative to the face 71 and diaphragm 57, and are mutually non-parallel. The non-parallel interior side walls such as the sloping surfaces 72 and 74 help prevent the symmetrical or parallel side wall configuration which might cause bouncing of waves back and forth in the cavity 56. Thus, a resonant cavity situation is avoided in this respect. Additionally, the upper interior surface or face 71 of the cavity 56 is sloped upwardly from the port to the passage 46 to that of the passage 44. The dome top face 71 is thus also not parallel to the diaphragm 57, which closes the cavity 56, to further deviate from a possible resonant cavity configuration. Thus, the cavity 56 is defined by interior dome surfaces which are generally mutually non-parallel, and generally disposed at varying angles relative to the diaphragm 57 in its relaxed configuration disposed across the opening of the cavity at the bottom face thereof. It is also noted that the entrance port to the passage 44 is thus farther from the diaphragm 57 than the entrance to passage 46, which can be a further factor in eliminating bubble formation.

In addition to the features described above, the problem of impedance mismatch can also be aggravated by the relative volumes of the cavity 56 and passages 44, 46. In order to minimize any impedance effect in this respect the passages 44, 46 are tapered in their construction from a larger diameter at their respective outer ends 76 to a smaller diameter where the passages intersect the cavity face 71 along the sloping side portions 74 and 72, respectively. In this way, the cross sectional area of the dome cavity 56 is insured as larger than the intersections of the passages with the cavity, thereby providing a minimized impedance change for pressure pulses entering the cavity from a passage and traversing the cavity toward a passage. The diameter of each such intersecting opening into the cavity 56 may be less than 0.080 inches and preferably about 0.050 inches to provide this feature.

The present invention thus provides a pressure dome which minimizes or avoids entirely problems and hazards which characterize prior art pressure domes utilized in the direct measurement of cardiovascular fluid pressure. Standing waves in the transmitter fluid are avoided by the asymmetrical arrangement of the walls and the diaphragm defining and closing the fluid accumulator cavity, respectively. The sloped, concave roof of the cavity disperses the fluid flow therethrough to the periphery of the asymmetrical walls to avoid the formation of bubbles in the transmitter fluid. Inaccuracies in the communication of cardiovascular pressure to the dome interior are further alleviated by the general truncated cone shape given to the passageways leading to and from the cavity to enhance impedance matching between the fluid flow lines and the cavity.

The foregoing disclosure and description of the invention is illustrative and explanatory thereof, and various changes in the size, shape and materials as well as in the details of the illustrated construction may be made within the scope of the appended claims without departing from the spirit of the invention.

I claim:

1. In a pressure measuring system for detecting pressure in the cardiovascular system of a subject, wherein fluid filled tube means are connected directly to portions of the cardiovascular system to directly interface with the blood supply of the subject and extend therefrom into fluid communication with pressure sensitive means for detecting fluid pressure, means for improving the response characteristics of the pressure measuring system, which means comprise:
   a. housing means including chamber means;
   b. deformable material means disposed across said chamber means to divide said housing means into first and second portions, said first portion being arranged for communication with said fluid filled tube means, and said second portion housing said pressure sensitive means; and
   c. fluid accumulator means formed in said chamber means in said first housing portion and adjacent said deformable material means wherein the surfaces defining said accumulator means are generally non-parallel, said fluid accumulator means comprising an internal cavity defined by interior surfaces in cooperation with said deformable material means, including a first interior surface generally opposite said deformable material means and peripheral surfaces between said first surface and said deformable material means, wherein:
      i. said first surface and said peripheral surfaces are non-parallel to said deformable material means in its relaxed configuration;
      ii. said peripheral surfaces are sloped at varying acute angles relative to said deformable material means in its relaxed configuration, and are mutually non-parallel; and
      iii. said first surface further comprises a convex surface portion for dispersing fluid flow within said cavity.

2. The apparatus of claim 1 further comprising at least two port means communicating with said cavity.

3. The apparatus of claim 2 further comprising tubular passage means connected with said port means and extending outwardly away from said cavity, said port means being generally arranged on opposite sides of said cavity.

4. The apparatus of claim 3 wherein said chamber means within said first portion of said housing means is in the form of a dome containing said internal cavity which is closed by said deformable material means, and said port means and connected tubular passage means are arranged to extend outwardly from said internal cavity through said dome.

5. The apparatus of claim 3 wherein said tubular passage means are generally truncated conical in form such that said passage means generally contract in cross section toward said cavity.

6. The apparatus of claim 2 wherein said port means are generally circular in configuration and have a diameter less than about 0.080 inches at the interface of said port means and said internal cavity.

7. Pressure measuring apparatus for use in measuring direct fluid pressure in a cardiovascular pressure measuring system, comprising:
   a. a housing including cover means closing one end thereof;
   b. deformable means separating said housing into first and second portions;
   c. said cover means having a cavity formed in said first housing portion, said cavity being formed at least in part by non-parallel interior peripheral walls and an upper internal surface between said peripheral walls;
   d. said deformable means closing the bottom of said cavity;
   e. a pair of passages extending through said cover means and communicating with said cavity for communicating fluid pressure thereto from a cardiovascular system; and f. wherein said peripheral surfaces are sloped at varying acute angles relative to said deformable means and said upper surface is non-parallel to said deformable means.

8. The apparatus of claim 7 wherein one of said passages intersects said cavity at a location closer to said deformable means than the location at which the other of said passages intersects said cavity.

9. The apparatus of claim 7 wherein the intersections of said passages with said cavity are generally circular and have an internal diameter of less than 0.080 of an inch.

10. The apparatus of claim 7 further comprising fluid dispersal means on said upper surface of said cavity.

11. The apparatus of claim 10 wherein said fluid dispersal means comprises a convex surface.

12. Fluid pressure responsive means comprising:
a. chamber means defined at least in part by peripheral surface means enclosed to one side thereof by top interior surface means, and closed to the other side by deformable material means;

b. passage means communicating with the interior of said chamber means by port means such that fluid may be accumulated in said chamber means and fluid pressure may be communicated through said passage means to said deformable material means; and c. wherein said top interior surface means is generally non-parallel relative to the orientation of said deformable material means, and said peripheral surface means are oriented at varying acute angles relative to said orientation of said deformable material means.

13. Fluid pressure responsive means as defined in claim 12 wherein said top interior surface means includes a generally convex surface portion, protruding into the interior of said chamber means for dispersing fluid flow therethrough.

14. Fluid pressure responsive means as defined in claim 12 wherein said passage means are generally truncated conical in shape so that the interior cross section of said passage means generally contracts toward said chamber means.

* * * * *